(12) United States Patent
Thompson et al.

(10) Patent No.: US 7,207,222 B2
(45) Date of Patent: Apr. 24, 2007

(54) ELECTROMAGNETIC PIEZOELECTRIC ACOUSTIC SENSOR

(75) Inventors: Michael Thompson, Toronto (CA); Scott Ballantyne, Newmarket (CA)

(73) Assignee: Sensorchem International Corporation, Toronto, Ontario (CA)

( * ) Notice: Subject to any disclaimer, the term of this patent is extended or adjusted under 35 U.S.C. 154(b) by 236 days.

(21) Appl. No.: 10/488,356

(22) PCT Filed: Aug. 28, 2002

(86) PCT No.: PCT/CA02/01320

§ 371 (c)(1),
(2), (4) Date: Nov. 29, 2004

(87) PCT Pub. No.: WO03/019981

PCT Pub. Date: Mar. 6, 2003

(65) Prior Publication Data

US 2005/0082944 A1    Apr. 21, 2005

Related U.S. Application Data

(60) Provisional application No. 60/375,436, filed on Apr. 26, 2002.

(30) Foreign Application Priority Data

Aug. 28, 2001 (CA) .................................. 2356044

(51) Int. Cl.
*G01N 29/00* (2006.01)
*G01N 29/04* (2006.01)
*G08B 3/02* (2006.01)

(52) U.S. Cl. ........................ 73/590; 73/649; 181/139
(58) Field of Classification Search ................. 73/649, 73/590; 181/139
See application file for complete search history.

(56) References Cited

U.S. PATENT DOCUMENTS

| | | | |
|---|---|---|---|
| 5,869,748 A | 2/1999 | Stevenson et al. | 73/53.01 |
| 2002/0076825 A1* | 6/2002 | Cheng et al. | 436/174 |
| 2006/0207330 A1* | 9/2006 | Adrian et al. | 73/632 |

FOREIGN PATENT DOCUMENTS

WO    WO 2004/109272 A1    12/2004

* cited by examiner

*Primary Examiner*—Hezron Williams
*Assistant Examiner*—Tamiko Bellamy
(74) *Attorney, Agent, or Firm*—Kathleen Marsman; Borden Ladner Gervais LLP (57) ABSTRACT

The invention relates to an electromagnetic piezoelectric acoustic sensor (EMPAS). The sensor comprises a piezoelectric sensor plate spaced apart from an induced dynamic electromagnetic field, such as from an electromagnetic coil through which AC current flows. The electromagnetic field induces vibration in the sensor plate by fluctuating the aligned dipole moments of the piezoelectric material. Changes on the surface of the sensor plate can be detected by variation in resonance frequency of the sensor plate. The invention represents an improvement over conventional sensor methodologies in that no metallization of the sensor surface is required, and no permanent magnet is needed. The sensor may be used to detect absorption of molecules or biomolecular interactions between probe and target molecules.

8 Claims, 9 Drawing Sheets

ELECTROMAGNETIC PIEZOELECTRIC ACOUSTIC SENSOR

This application claims priority from Canadian Patent Application No. 2,356,044 filed Aug. 28, 2001, and from U.S. Provisional Patent Application 60/375,436 filed Apr. 26, 2002. The content of both documents is incorporated by reference herein.

FIELD OF THE INVENTION

The present invention relates generally to an acoustic wave sensor, and particularly to an acoustic sensor incorporating piezoelectric material.

BACKGROUND OF THE INVENTION

Acoustic wave transducers are conventionally divided into bulk acoustic wave (BAW) and surface acoustic wave (SAW) devices. The majority of BAW devices employ a 0.2 to 0.5 mm thick AT-cut quartz resonator disc coated with metal electrodes, such as gold electrodes, on either side of the disc. A high frequency (low MHz) sinusoidal voltage is applied across the gold electrodes causing the quartz resonator disc to oscillate at its resonant frequency. When used as a mass sensor, this device is referred to as a quartz crystal microbalance (QCM). The quartz crystal microbalance has become widely used as a biosensor.

Piezoelectric material consists of atoms and/or molecules which all have their dipole moments aligned in the same direction within a lattice. If an outside force is applied to the lattice in such a way as to shift the alignment of the dipole field alignments, a voltage is produced. In the case of conventional QCM devices, the quartz crystal serves as the piezoelectric material, and the outside force comprises an alternating high frequency sinusoidal voltage applied to metal electrodes coated on the quartz crystal disc. The stringent conditions under which such quartz crystal discs are produced results in very reproducible discs and, therefore, reliable results.

However, conventional QCM acoustic transducers have a number of limitations. There is a strict requirement to photolithographically apply a metal film onto the disc of piezoelectric material. Additionally, hard wire connections to the metal film are required. Conventional QCM devices have a detection limit of approximately 1 ng/mL, which is inadequate for the monitoring of low molecular weight biomolecules. All of these problems impede the development of a practical acoustic sensor based on conventional QCM technology.

A new acoustic sensor, the magnetic resonance sensor (MARS), has recently been developed which offers an alternative to the QCM device. This technology has been described, for example, by Stevenson et al. in U.S. Pat. No. 5,869,748, issued Feb. 9, 1999. The MARS transducer described by Stevenson et al. establishes an acoustic resonance in a free-standing metallized silica glass plate using remote magnetic and electromagnetic fields. The device exploits magnetic fields for generation of acoustic waves in a thin metal film coated on one side of the silica glass plate. A coil connected to a RF generator, and a permanent magnet are placed on one side of the metallized silica glass plate. The magnet is not in direct contact with the plate and is thus said to be "remote" from the plate, although the induced magnetic fields extend to the plate. The magnetic fields achieve excitation of ions within the metallized coating on the plate. Unlike other previously designed electromagnetic-acoustic transduction sensors (EMATS), the transduction efficiency of the MARS device benefits from both electrical and acoustic resonance effects.

When exposed to an electromagnetic field, acoustic waves are produced in a metal film as a consequence of the radial Lorentz forces generated within the film. These "non-contact" forces are then conveyed, through momentum caused by contact of the metal film with a silica glass plate, to achieve acoustic resonance in the glass plate. The process is described by equation 1, where the Lorentz forcing term, F(z), is coupled to differential terms representing the elastic properties of the silica glass plate:

$$\frac{\partial^2 u}{\partial t^2} - V_s \frac{\partial^2 u}{\partial x^2} = \frac{F(z)}{C} \quad (1)$$

where C is the elastic modulus of the silica glass plate; u is the particle displacement; and $V_S$ is the shear velocity. Because only one side of the glass plate is being driven, both the asymmetric and symmetric standing waves can be supported by a plate of thickness d, where the acoustic wave vector, k, is equal to ρm/d, where m is an integer. The resonance frequency, $f_R$, can be calculated from the following equation:

$$f_R = \frac{mV_S}{2d} \quad m = 1, 2, 3, \ldots, n. \quad (2)$$

The resonance frequencies occur at harmonics of the fundamental frequency (m=1) and occur twice as often in a device such as the MARS device as compared to a QCM device.

Acoustic wave generation in the metallized silica glass plate is associated with a radio frequency generated in the coil, in the order of 10 s of mAs. The current gives rise to a series of voltage dips, on the order of mVs, at frequency intervals corresponding to the harmonic series of standing waves. The voltage dip corresponds to an acoustic resonance because the coil receives reflected RF power from the metal film that reduces in value when acoustic power is generated. The received signal voltage can be described by the following equation:

$$V = \frac{GB^2 I Q_e}{\rho V_S (1+\beta)} * \frac{2}{\alpha d} \quad (3)$$

where V is the received signal voltage; B is the magnetic field; I is the source current; $Q_e$ is the quality factor for the parallel resonant circuit; ρ is the density of the glass plate; $V_S$ is the shear velocity for the acoustic wave; α is the attenuation coefficient; d is the thickness of the plate; and β is an adjustment factor for phase differences that may exist across the metal film.

The MARS system offers advantages over the established QCM systems. From the above equation, it is clear that the received signal voltage can be increased through a variety of routes, such as by increasing the magnetic field strength, or by increasing the source current. An applicable source current frequency may range from the low MHz range up to around 60 MHz. However, the MARS system requires both a permanent magnet and electromagnetic field generation from the coil in order to induce appropriate movement within the metal film which then induces vibration in the plate.

The MARS device involves only indirect generation of vibration in the silica glass plate because only the metal film is initially caused to vibrate due to the magnetic and electromagnetic fields. The momentum from the vibration of the metal film is then imparted to the lattice of the silica glass plate. Thus, the glass plate is caused to vibrate only indirectly because of its proximity adjacent to the metal film. Because the sensing portion of a MARS device is indirectly caused to resonate through vibration of the metal film, a MARS sensor induces indirect generation of vibration in a sensor, and does not incorporate electromagnetism.

The above-described MARS device suffers from problems arising from reproducibility. Because resonance occurs in both the metal film and the silica glass plate, inconsistencies in the shape, thickness or density of either the film or the plate will effect the resulting vibration of the plate, and the shape of the acoustic resonance. The shape of the acoustic resonance for either symmetric or asymmetric modes can be effected. If an acoustic response does not appear to be a single peak, but rather as a doublet, at lower frequencies, or multiple peaks clustered around a main central resonance, this suggests that the glass plate faces are not parallel, or that they are acoustically isotropic. Inconsistencies in the plate complicates the results obtained from the MARS sensor because a shear wave generated in the metal film does not travel in a single dimension. Instead the glass plate supports the generation of lateral waves, requiring the incorporation of a more complex three-dimensional resonator model to account for the distorted resonance envelope. Thus, inconsistencies in plate shape, thickness or density introduces a significant amount of error when comparing the results obtained using different silica plates. From equation 3, it is clear that differences in plate thickness (d), non-parallel plate faces ($\beta$, $V_S$, $\alpha$) and plate density ($\rho$, $\alpha$, $V_S$) profoundly affect the received signal voltage.

Although the MARS device traverses the requirement of QCM systems to photolithographically apply a metal film electrode onto a specially polished crystal of piezoelectric material, metallization of the silica glass plate is still required, and new problems associated with reproducibility in the plate specifications are introduced.

Transverse shear mode acoustic wave sensors have been used in an increasing number of applications over the past number of years. The sensors employ a piezoelectric (usually quartz) disc as the transducing element. The sensors generate specific forms of mechanical resonance in the substrate, resulting in acoustic waves propagating in different directions. To do this, thin slices are cut from single crystal quartz (for example) at specific orientations with respect to the crystallographic axis. The geometry of the final slice defines the boundary conditions, while the orientation defines the values of the different matrices. When combined with the wave equations, they lead to solutions, which describe the different possible piezoelectric device structures and their behaviour[1].

Sauerbry presented a relation between the amount of mass deposited onto a quartz crystal surface and its resonant frequency[2]. Now it is known that the quartz crystals are not only sensitive to mass, but also to coupling between the crystal and its surrounding environment[3]. To make the crystal sensitive to specific chemical species, coatings that bind or adsorb the analytes of interest may be applied.

The development of transverse shear mode sensors is currently impeded by a number of factors. For example, metal electrodes must be applied to the crystal, which increases the complexity of the chemistry required to immobilize selective films. Hardwire connections must be made to the electrodes, which may disrupt the flow of liquid through the cell. Ideally, detection and chemistry should be separated. Further, the detection limit of approximately 1 ng/mL is often inadequate for monitoring low molecular weight biomolecules. Additionally, there are difficulties involved in adapting such a sensor to work at higher frequency modes, in order to increase sensitivity. There is a need for a sensor that eliminates one or more of the above-noted problems.

It is, therefore, desirable to provide a sensor device which incorporates electromagnetic generation of vibration within a sensing portion of the device, and which is less susceptible to variability than the above-noted MARS technology.

SUMMARY OF THE INVENTION

It is an object of the present invention to obviate or mitigate at least one disadvantage of previous acoustic wave sensors.

The invention provides an ElectroMagnetic Piezoelectric Acoustic Sensor (or "EMPAS"), which traverses at least one disadvantage of previous sensors. The inventive sensor remotely induces acoustic waves in a sensor plate, which may be a mounted piezoelectric disc.

The invention provides an acoustic wave sensor comprising a sensor plate formed of piezoelectric material, an electromagnetic field fluctuator for inducing a fluctuating electromagnetic field in the piezoelectric material, thereby causing acoustic wave vibration of the sensor plate, and a monitor for evaluating vibration of the sensor plate. Thus, the sensor according to the invention remotely induces acoustic waves in a mounted piezoelectric sensor plate.

In a further embodiment, there is provided a method of evaluating biomolecular interaction of a probe with a target comprising the steps of (a) tethering the probe to a sensor plate formed of piezoelectric material, (b) imparting a fluctuating magnetic field to the piezoelectric material so as to vibrate the piezoelectric material at resonance frequency; (c) exposing the sensor plate to a composition suspected of containing the target; and (d) evaluating changes in vibration of the piezoelectric material caused by interaction of the probe with the target.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein.

DETAILED DESCRIPTION

Generally, the present invention provides an acoustic wave sensor incorporating piezoelectric material. The acoustic wave sensor comprises a sensor plate formed of piezoelectric material, an electromagnetic field fluctuator for inducing a fluctuating electromagnetic field in the piezoelectric material to cause acoustic wave vibration of the sensor plate, and a monitor for evaluating vibration of the sensor plate. The fluctuator is preferably formed from a coil through which AC current flows to induce a fluctuating electromagnetic field.

A biosensor may be formed from the acoustic wave sensor, in which case, a biomolecule may be bound to the sensor plate. Such binding may take the form of a means such as tethering, covalent binding, non-covalent adhesion, adsorption, or ionic bonding.

The invention also relates to a method of evaluating biomolecular interaction of a biomolecule with a piezoelectric sensor plate comprising the steps of imparting a fluctuating electromagnetic field to the piezoelectric sensor plate so as to vibrate the plate at a resonance frequency; exposing the sensor plate to a composition suspected of containing the biomolecule; and evaluating changes in vibration of the piezoelectric sensor plate caused by interaction of the biomolecule with the sensor plate.

The invention also relates to a method of evaluating biomolecular interaction of a probe with a target comprising the steps of: binding the probe to a sensor plate formed of piezoelectric material; imparting a fluctuating electromagnetic field to the sensor plate so as to vibrate the sensor plate at a resonance frequency; exposing the sensor plate to a composition suspected of containing the target; and evaluating changes in vibration of the sensor plate caused by interaction of the probe with the target.

The electromagnetic field fluctuator is used to impart vibration to the piezoelectric material at resonance frequency. The fluctuator may comprise a coil electromagnet, such as a copper coil wire that may optionally be coated with enamel. Such a coil is exposed to alternating AC current. By modulating the current through the coil, fluctuation of the aligned dipoles in the piezoelectric material is induced.

The use of a permanent magnet is not required with the invention, since the fluctuator imparts adequate energy to the piezoelectric material to generate resonance vibration. In the case where a coil serves as a fluctuator, electromagentic energy from the coil is modulated so as to cause vibration within the piezoelectric material. However, a permanent magnet could be used in addition to the fluctuator, if the effect of including a permanent magnet is deemed desirable for any reason. The effect of a permanent magnet on piezoelectric material would serve to shift the alignment of the dipole moments within the piezoelectric material in a static (non-fluctuating) manner, which would not in itself cause vibration in the material. This may be desirable, and thus it is conceived that a permanent magnet may be a component included within the fluctuator or used in addition to the fluctuator according to the invention. The presence of a fluctuator, such as a coil through which AC current flows, causes dynamic (fluctuating) movement of the aligned dipole moments within the material, thereby producing vibrations in the material. In the prior art MARS technology, such dynamic fluctuations from an electromagnetic coil alone would not be adequate to induce vibration in the metallized silica glass plate.

According to the invention, the fluctuator is placed in a location adequately spaced from the sensor plate so as to allow appropriate induction of a fluctuating field. The fluctuator is placed close enough to ensure vibration is imparted, but not so close that the signal from the vibration is reduced to "noise". The appropriate distance can easily be determined for different sized sensor plates by observing the signal generated, and the distance can be optimized by observing the output signal.

The sensor device may be used as a biosensor with which behavior of biological molecules (such as proteins, DNA, RNA) can be determined. Further the device can be used to evaluate "chemisorption" of compounds onto a tailored substrate surface, or "physisorption", in terms of surface characteristics. For example, salinizing ligands may be used to convert surfaces to hydrophilic or hydrophobic states. Non-covalent attachment of a molecule of interest to a sensor surface may be employed to determine such features as biocompatibility of polymers or coatings, for example silicon or other polymers representative of implants requiring biocompatability.

The device may be used to evaluate immunochemistry (antibody-antigen interaction) through covalent immobilization of molecules to a surface of the device. Drug candidates, small molecules, nucleic acids, and cells, such as bacterial cells or platelets may be bound to the surface of the sensor. Advantageously, the piezoelectric material may be easier to immobilize such molecules or cells onto than gold or other metallics.

The device is useful for detecting of biological molecules, such as in DNA hybridization, immunochemical interactions, and nucleic acid drug interactions. In this context, the invention also relates to a method of evaluating biomolecular interaction of a probe with a target.

As used herein, the terms "probe" and "target" refer to molecules capable of specific interaction with each other. These may be referred to herein as the probe/target pair. The probe is a molecule that is tethered, bound, adsorbed to or is in some form of permanent or temporary contact with the sensor surface. The target is a molecule capable of interaction with the probe, but which is not bound to the sensor surface. For example, one of the probe/target pair may comprise a nucleotide sequence to which the other of the probe/target pair is complementary. Further, the probe/target pair may be an antibody/antigen pair, a protein/small molecule pair, or any number of biological molecules capable of specific interaction with each other. Specific interaction may comprise, for example: binding, adsorbence, adherence, or hybridization.

The method of evaluating probe/target interaction comprises the steps of tethering the probe to the sensor surface. This can be done in a variety of ways. An exemplary method for high surface density covalent immobilization of oligonucleotide monolayers is described by Thompson et al. in U.S. Pat. Nos. 6,159,695 and 6,169,194, issued on Dec. 12, 2000 and Jan. 2, 2001, respectively. Of course, any acceptable method of tethering can be utilized with the invention.

In the case where probe-target interaction is to be assessed using the sensor, the sensor surface is then exposed to a test composition suspected of containing the target. This may be, for example, an aqueous solution comprising a diluted or non-diluted amount of a test sample. The test sample may be derived from any source to be tested for the presence of the target. For example, the test sample may comprise a biological fluid or a homogenized, purified, and/or diluted biological tissue. Should the target be present in the composition, interaction between the target and the probe occurring on the sensor surface will effect the vibration of the piezoelectric material in a detectable manner.

According to the invention, a fluctuating electromagnetic field is imparted to the piezoelectric material so as to vibrate the piezoelectric material at resonance frequency. This fluctuation can be induced by using a coil electromagnet, such as a copper coil wire that may optionally be coated with enamel. Such a coil is exposed to alternating AC current. By modulating the current through the coil, fluctuation of the aligned dipoles in the piezoelectric material is induced.

The turn density of the coil and the size of the wire used in the coil may vary and may be altered to achieve the desired effect. To scale-up the sensor, a number of coils may be placed separately in appropriate proximity to a larger sized sensor, or a variety of different means may be used, as would be clear to one of skill in the art.

By evaluating changes in vibration of the piezoelectric material caused by interaction of the probe with the target, information can be derived to determine the quantity and/or quality of the probe present in the test composition.

Detection of the frequency change due to the occurrence of a bio-recognition or bio-interaction event is achieved by specific signal processing methods. The actual output signal is comprised of a high frequency carrier (in the order of 10's of MHz, for example from 10 to 100 MHz, such as a frequency of 81 MHz), modulated by a low frequency signal (for example, about 1 kHz). This complex signal is filtered using specific RC circuits to remove: 1) the carrier signal and modulation to obtain the offset baseline; and 2) the carrier signal only. By subtracting the above signals 1) and 2) with offset removal, useful information contained in the amplitude of the modulation is isolated and then further amplified.

Figure 1:
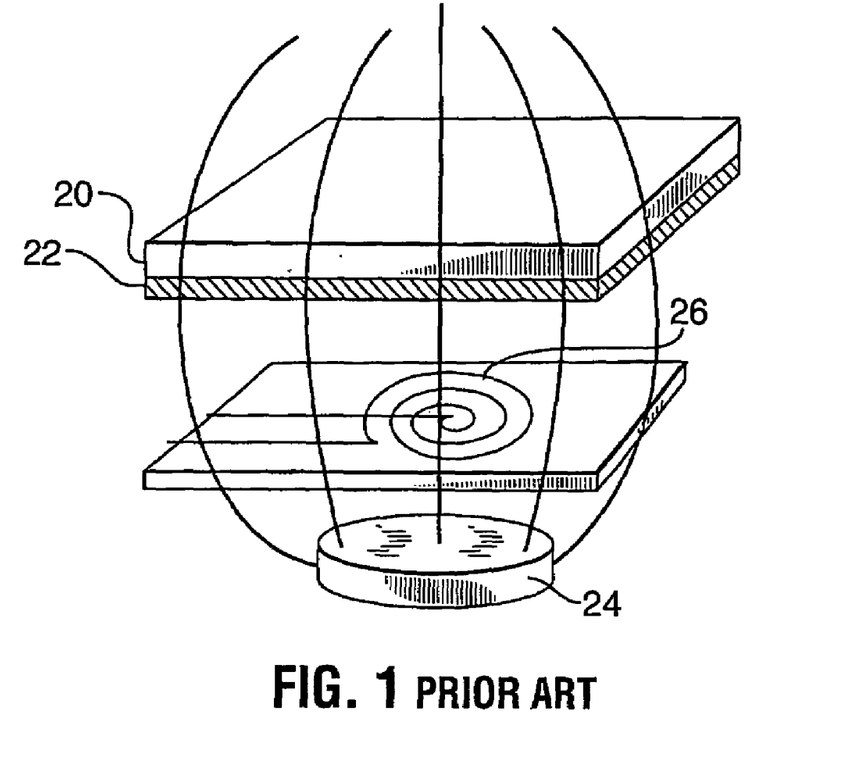
FIG. 1 is a schematic illustration of a PRIOR ART acoustic wave sensor according to MARS technology, incorporating a permanent magnet, an elecromagnetic coil, and a metallized silica glass plate.

FIG. 1 depicts a PRIOR ART sensor according to the MARS technology. A silica glass plate (20) having an aluminum film (22) coated thereon is exposed to a permanent magnet (24) and an electrical coil (26). The electrical coil (26) has oscillating current passing therethrough to induce oscillating eddy currents in the aluminum film (22) through movement of electrons in the film. In this example of prior art, the fields induced by the permanent magnet (24) and the electromagnetic coil (26) are perpendicular. Both the permanent magnet and the electromagnetic coil are required in this apparatus. The vibrations induced in the film (22) cause vibration of the silica glass plate (20) because of the contacting proximity of the film to the plate.

Figure 2:
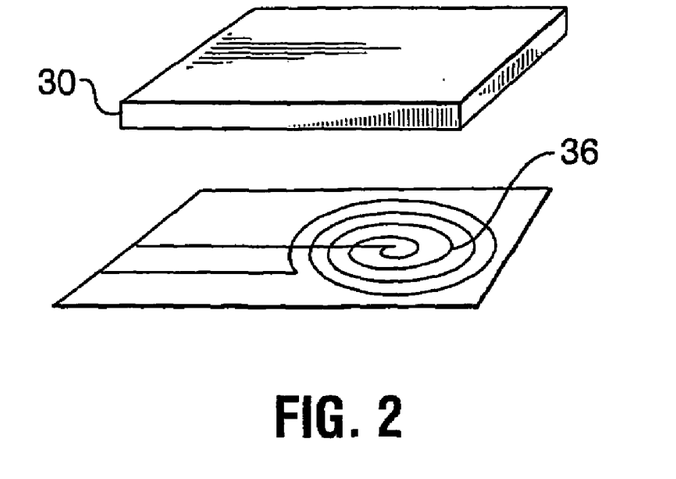
FIG. 2 is a schematic illustration of an acoustic wave sensor according to the invention.

FIG. 2 provides a schematic illustration of a sensor according to the invention. A sensor plate (30) formed of AT-cut quartz is placed in proximity to a copper wire coil (36), through which AC current flows. The electromagnetic fields generated from the coil shifts the alignment of the dipole field alignments in the quartz crystal sensor plate, thereby inducing resonance in the crystal. Notably, the invention does not rely on vibration of a metal coating to cause vibration, and in this way can be considered to induce vibration directly. Vibration of the sensor plate (30) is evaluated by a monitoring device, not shown, which derives feedback from the coil.

Quartz is the most common crystallographic material employed currently in piezoelectric applications, particularly in chemical and biosensor technology. However, other materials are available that possess piezoelectric properties, and in certain cases, superior electric or magnetic field-to-mechanical coupling (Q-factor) is displayed. Included in this category are lithium niobate and gallium phosphate ($GaPO_4$). A higher Q value leads to higher analytical sensitivity. These other piezoelectric materials would be suitable for use with various embodiments of the invention.

According to the invention, the piezoelectric crystal plate itself is directly vibrated, not vibrated merely because of intimate contact with a metallized component, such as the metal film in MARS technology. The invention reduces problems associated with distortion of the wave travelling through the metal film. Further, by negating the requirement for application of a metal film on the sensor, cost is reduced and variability between crystal plates is decreased. In the inventive sensor, the use of a permanent magnet is not required (but is optional), which reduces the cost of the sensor components.

The invention is advantageous over traditional QCM sensor technology because the piezoelectric material does not require a metal film coated thereon, nor electrodes in contact with the film. This significantly reduces manufacturing costs of the piezoelectric material, which for QCM is often in the form of a disc having gold film electrodes coated thereon.

The vibration of a piezoelectric crystal plate in an electromagnetic field causes resonance vibration in the plate. If an electromechanical coupling constant and electric field are substituted for the forcing term in equation (1), an equation of the same form for the piezoelectric generation of acoustic waves appears. Thus, the invention incorporates electromagnetic generation of vibration in the piezoelectric material, and produces similar conditions for the production of acoustic waves as compared to QCM.

Advantageously, the invention incorporates the fluctuating magnetic fields from electromagnetic having AC current flowing therethrough. The fluctuation is caused to an extent adequate to shift the alignment of the dipole field alignments, thereby inducing resonance. By exciting resonance in the piezoelectric crystal, the device utilizes an electromagnetic generation event.

Figure 3:
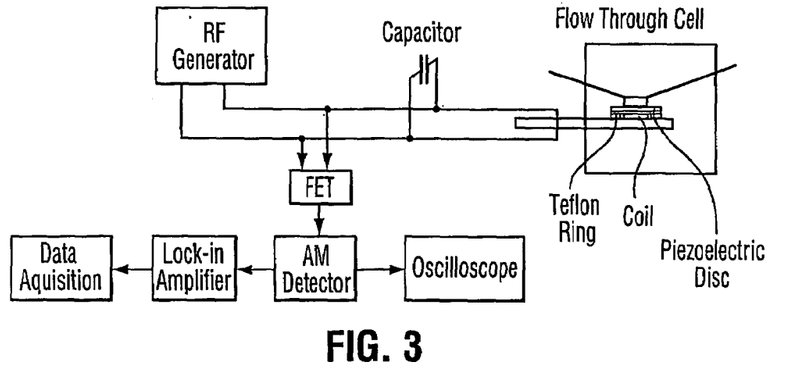
FIG. 3 provides a block diagram of a device according to the invention.

FIG. 3 provides a block diagram of a device according to the invention. The device comprises a number of components, each of which is discussed in more detail herein.

The RF generator in this example is a Hewlett Packard (HP 8648B) RF signal generator that applies a frequency 30+ MHz with an FM modulation around 10 kHz. The signal is further modulated by approximately 912 Hz by the function generator on the lock-in amplifier. The carrier signal is used to excite resonance in the piezoelectric disc.

The capacitors for use with the invention are, in this example, silver-mica capacitors, obtained from Newark Electronics, having capacitances varying from 15 up to 68 pF. Variable Air Gap Capacitors (Electrosonics) may be used with a range of 10 to 80 pF. The capacitor is connected across the terminals of the coil in order to tune the circuit to electrical resonance.

The coil consists of enamelled copper wire (outside diameter approx. 90 µm) wound into a flat spiral (approx. 4 mm diameter) on an epoxy laminate board. The coil serves to generate the required electric/magnetic field to force the crystal into resonance.

The piezoelectric crystals used in this example are quartz discs having a diameter of 0.538". The crystals have a 9.0 MHz fundamental frequency. Electrodes (0.201" diameter) on either side of the crystal face consist of a 50–100 angstrom chromium adhesion layer, covered by a 1000 angstrom gold layer. The crystal is suspended above the coil with a 30 µm gap between them.

The invention also may include an oscilloscope, such as a Tektronix™ TDS210 scope, which is mainly used for diagnostic purposes. A lock-in amplifier, such as the Stanford Research Systems, model SR510 lock-in amplifier, is locked on the 912 Hz modulation rate to reduce noise and to further amplify the signal. A program such as the National Instruments Labview Windows Program™ v 6.0 may be used with the invention. Programs written with this software can be used to control the settings on both the signal generator and lock-in amplifier via the GP-IB card. Programs include one for scanning the resonance envelope and one for monitoring frequency shifts after biomolecule injection.

Figure 4A:
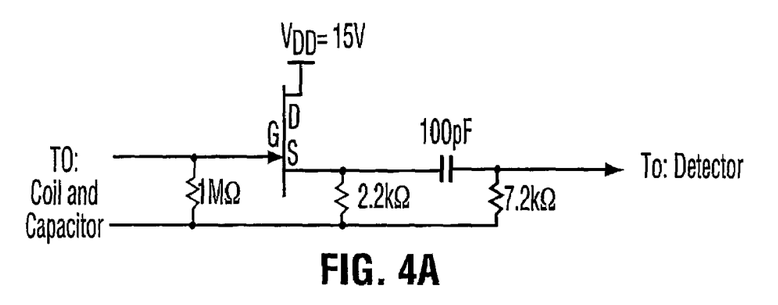
FIG. 4A is a schematic diagram of an exemplary field effect transistor for use with the invention.

FIG. 4A schematically illustrates one possible field effect transistor for use with the invention. The field effect transistor serves, in part, as a firewall between the detector and resonant circuit. A 15V power source is depicted in FIG. 4A. The power source serves to power the detector and field effect transistor.

Figure 4B:
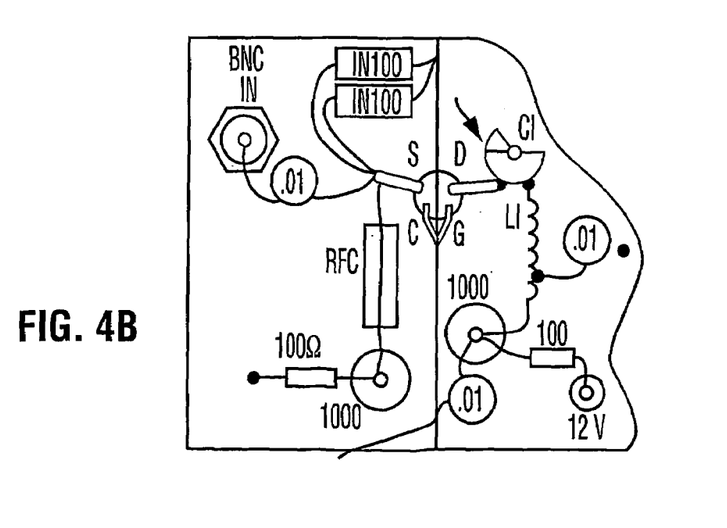
FIG. 4B is a schematic diagram of a alternative exemplary field effect transistor for use with the invention.

FIG. 4B provides a schematic of another possible field effect transistor for use with the invention. The field effect transistor can serve as a "firewall" between the detector and resonant circuit.

Figure 5:
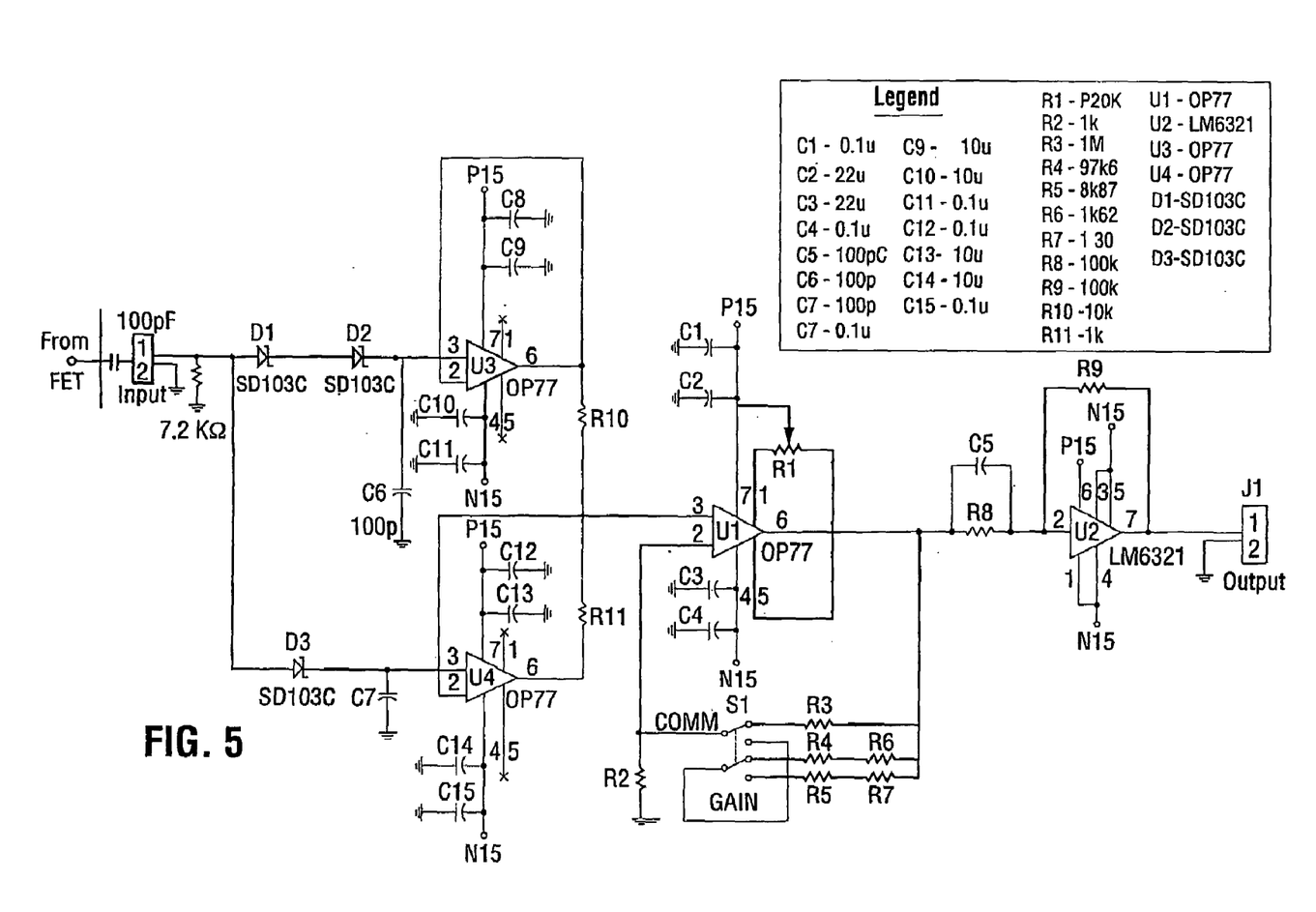
FIG. 5 provides a schematic diagram of the AM detector.

FIG. 5 schematically illustrates the AM detector. The AM detector serves to remove the high frequency (MHz) carrier signal and to amplify the low frequency (Hz) modulation signal.

Figure 6:
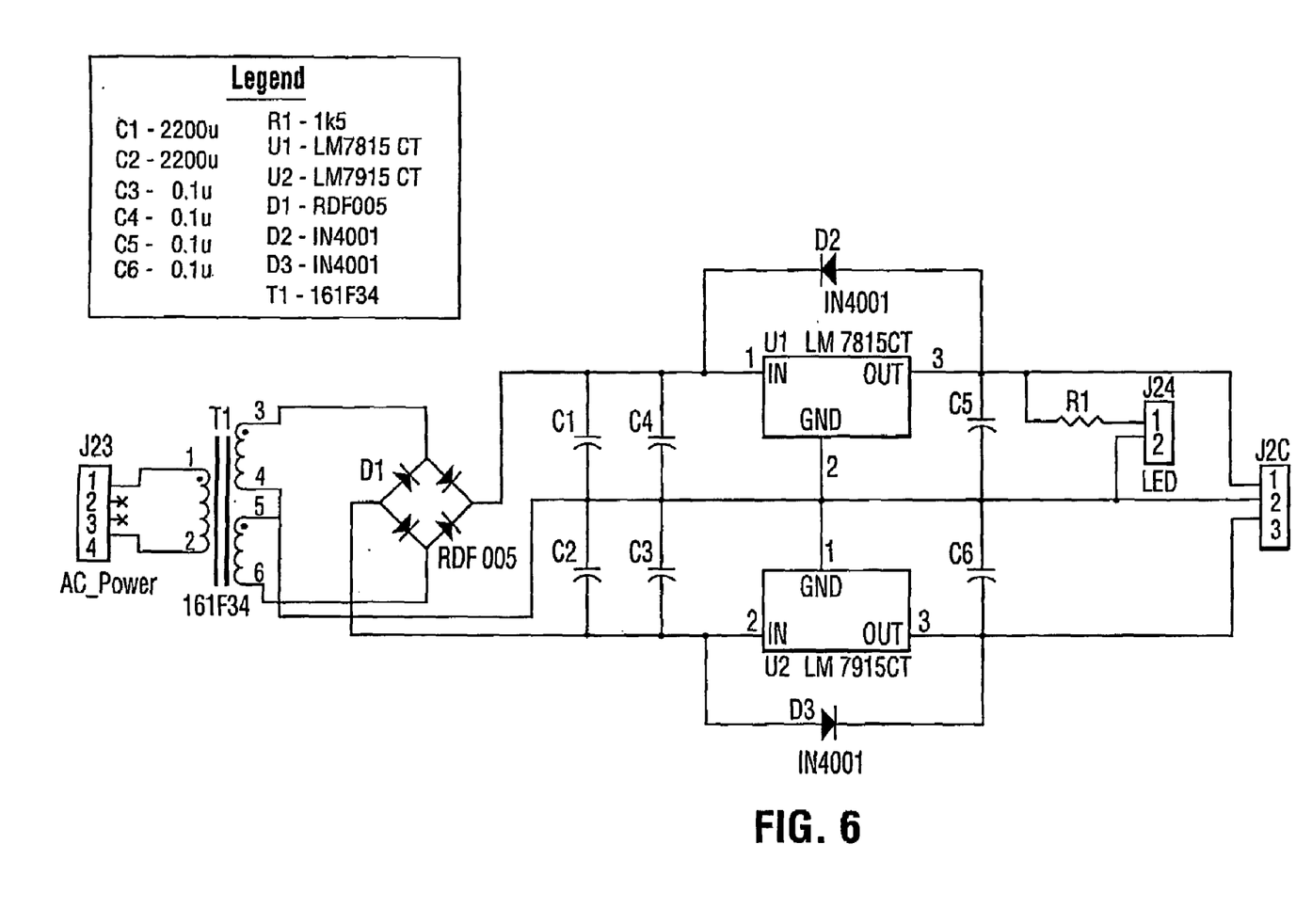
FIG. 6 is a schematic diagram of a 15V power source for use with the invention.

FIG. 6 illustrates an exemplary power source for use with the invention. The power source serves to power the detector and field effect transistor, and in this figure is shown as a 15 V power source.

Device theory applicable to the inventive device is provided as follows. It is to be understood that a mechanism put forth herein should be in no way limiting to the invention. When the coil capacitor circuit is tuned to electrical resonance, the resonator experiences the largest energy field possible that the coil could produce at that particular driving frequency. The excitation mechanism for resonance, that is, how the resonance is generated in the disc, may be attributable to the mechanism of piezoelectricity. However, this theory in no way limits the invention to this mechanism.

Compression of a piezoelectric material in one direction results in an increased polarization or charge separation between electropositive and electronegative atoms. By carefully choosing the direction of the compression with respect to the crystallographic axes, one can create a difference in surface potential across the material. These effects are observed when the crystalline material lacks central symmetry. Therefore, only certain materials belong to specific crystal classes and point groups demonstrate the piezoelectric effect.

In classical transverse shear mode acoustic wave devices, mechanical resonance is generated by a momentary voltage pulse, which is applied to the center of the disc causing an initial displacement. The quartz has both elastic and viscous properties, therefore the mechanical displacement will lag behind the voltage pulse. This mechanical displacement stores potential energy, which is then converted to kinetic energy. The magnitude of the displacement and the maximum velocity of a particle with respect to the point of application will be dictated by the dimensions and properties of the quartz plate and the direction of the applied field[4].

$$\rho \frac{\partial^2 u}{\partial t^2} = q_m \frac{\partial^2 u}{\partial x^2} + F \frac{\partial^3 u}{\partial x^2 \partial t} \qquad (4)$$

wherein u is the particle displacement; t is time; x is a coordinate; p is the density of the quartz; $q_m$ is the stiffness coefficient; and F is the field strength.

The piezoelectric nature of the material results in the production of a time varying electric potential, which is in phase with the mechanical displacement[4]. This time varying potential is then coupled into the system, thereby acting as a driving force in the resonance process. However, this particle motion will be damped by the quartz's viscosity, and will therefore decay with time. In conventional QCM devices, to maintain resonance, a high frequency (low MHz) sinusoidal voltage is applied to the electrodes on either side of the piezoelectric disc. The efficiency of the coupling of mechanical vibrations with the outside electric field and the colinearity of phase and group velocity as well as the directions of the applied electric field must be considered[5].

The efficiency of coupling is assessed by the piezoelectric coupling factor[5].

$$k^2 = \frac{d_{in}^2}{\varepsilon_1 s_{nn}^E} = \frac{\pi^2}{4} \times \frac{\Delta f}{f_m} \qquad (5)$$

wherein $\varepsilon_1$ is the effective permitivity; $d_{in}^2/s_{nn}^E$ is $1/\varepsilon$ which is the effective piezoelectric strain constant; $\Delta f$ is the difference between resonant and anti-resonant frequencies; and $f_m$ is the frequency for maximum admittance.

Higher $k^2$ values generally indicate a stronger piezoelectric effect in the form of wave generation efficiency[6]. This illustrates that acoustic vibrations can be set-up when an outside radio-frequency (RF) electric field is applied to the material. In the case of the EMPAS device described herein, the electric field generated by the coil remotely excites and maintains acoustic resonance in the piezoelectric plate suspended close by.

Once resonance is established the device can be used as a sensor because, around the resonant frequency of the disc, the impedance of the coil changes rapidly over the entire resonance envelope (see FIGS. 7 to 9 and 13 to 15). Thus any change in the properties of the plate (mass, viscosity, slip, roughness, surface free energy) will cause a shift in the resonant frequency of the disc[7]. Any change in the resonant frequency of the disc will be associated with a change in the impedance of the coil, which will indicate something on the surface has changed. The purpose of the described detection scheme is therefore designed to monitor the impedance changes in the coil, which reveals changes happening on the surface of the device.

With respect to an embodiment of the inventive sensor described herein, the fluctuating magnetic field set up by the coil could excite acoustic waves in a thin film of chromium. The acoustic waves generated in the metal would serve as a compressive force to set up the polarization across the surface of the piezoelectric substrate. Providing the magnetic field is fluctuated around the desired excitation frequency, this mechanical motion (hence resonance) can be maintained.

EXAMPLE 1

Methodology. Resonance envelopes were generated in air and liquid by soft clamping a crystal (an AT cut quartz disc having a gold electrode thereon) in a flow through cell (internal volume approx. 70 μL). Resonance envelopes generated in liquid were acquired in Tris buffer (7.5 pH); prepared by adding 5 mL of 1 mol/L Tris+7 mL 5 mol/L NaCl+0.2 mL of 0.5 mol/L EDTA+487.8 mL distilled water. Flow rates were maintained at approximately 0.6 mL/min. In this example, the field effect transistor is of the type shown in FIG. 4A.

Protein injection experiments involved the use of neutravidin (non-glycosylated version of avidin). The neutravidin was dissolved in the tris buffer to make a 1 mg/mL solution. Buffer was flown through the cell for 10 minutes, then 500 μL of the neutravidin solution was injected, followed by flowing buffer. All experiments were conducted using 45 MHz carrier signal. Data was processed and displayed via NI Labview™ program software.

Figure 7:
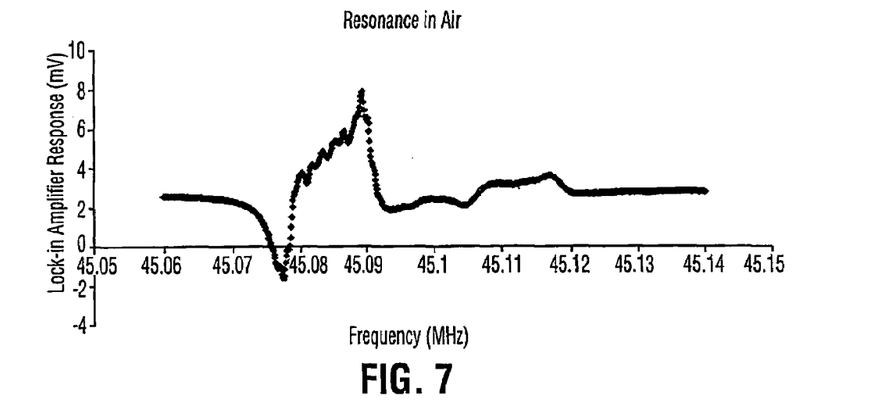
FIG. 7 is a resonance envelope chart for crystal operating in air.

Results. FIG. 7 shows the resonance envelope for an AT-cut quartz disc excited in air. The shape of the envelope indicates that a number of different resonance modes are being excited simultaneously. It is believed that numerous modes are being excited because the center of the coil is not positioned perfectly underneath the center of the disc. The shape of the coil, due to the hand winding process, is not symmetrical which would have a direct influence on the shape of the field (magnetic or electric) that is responsible for the excitation process.

Figure 8:
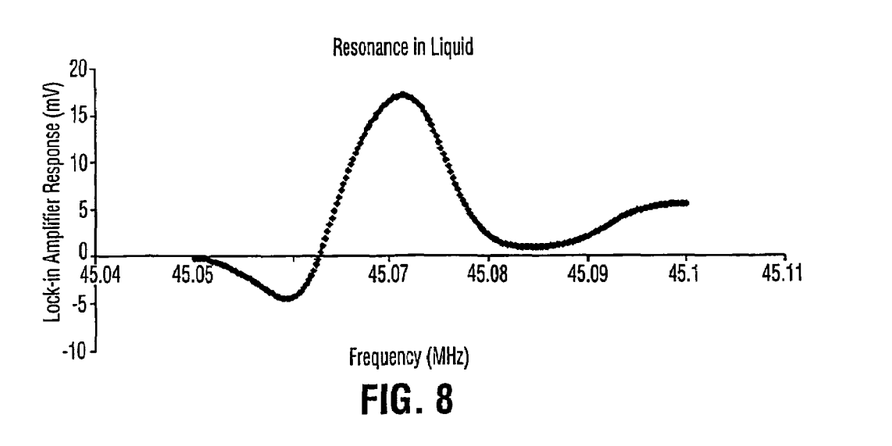
FIG. 8 is a resonance envelope chart for crystal operating in liquid (tris buffer).

Upon immersing that same disc in liquid (Tris buffer) the resonance envelope, as depicted in FIG. 8, changed to a smoother curve, at slightly lower frequencies. The reason for this change in appearance is likely due to the coupling between the oscillators surface and the liquid medium, thereby resulting in a so called "smearing effect" where the modes are simply smeared together, making it look as though a single mode is being excited. The reason for the shift to lower resonant frequencies is also due to coupling phenomena. Together, along with viscosity and coupling effects, the change in the pressure acting on the surface of the oscillator accounts for the shift to lower resonant frequencies.

For the protein injection experiments, neutravidin (non-glycosylated form of avidin) was chosen for a series of experiments. Avidin is used widely in bioanalytical chemistry to immobilize biological species, such as nucleic acids, to substrates through the strong bond it forms with the biotin moiety (RNA and DNA are routinely synthesized with a biotin moiety on the 5' or 3' end of the chain to facilitate immobilization)[8]. Avidin is a basic homotetrameric glycoprotein having a total mass of about 67 to 68 kDa. The protein possesses a disulfide bond in each subunit and is adsorbed readily onto gold via a metal-sulfur interaction[8]. Neutravidin does not contain any carbohydrate residues, is about 60 kDa, and binds biotinylated species with approximately the same affinity as the parent avidin molecule.

Figure 9:
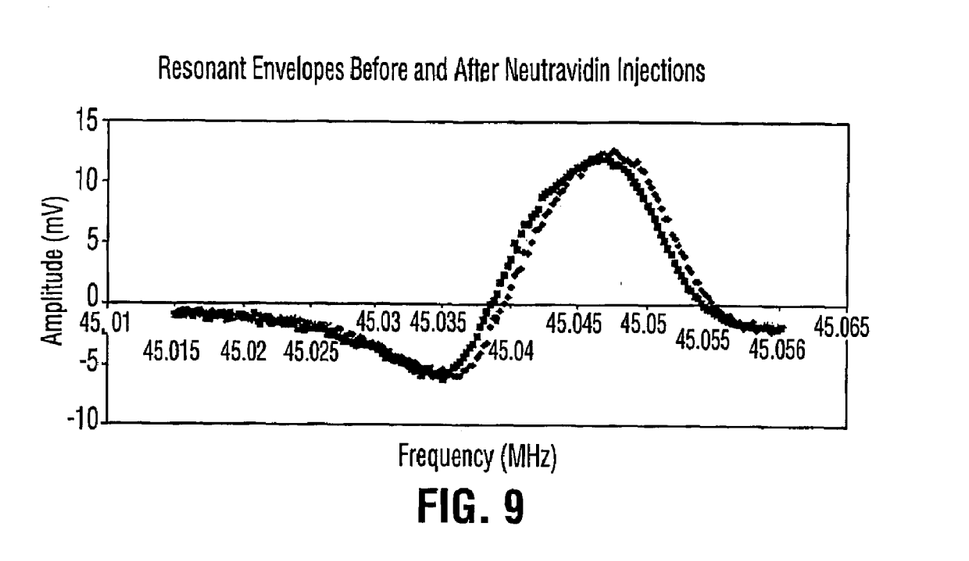
FIG. 9 is illustrates resonance envelopes before (series 1—diamonds) and after (series 2—squares) injection of neutravidin.

FIG. 9 depicts resonance envelopes acquired before and after neutravidin injection. Series 1 (represented with diamonds) is the resonance envelope acquired in flowing buffer solution only while series 2 (represented with squares) is the resonance envelope taken about 20 minutes after protein injection. There is clearly a downshift in the resonance curve as a result of the presence of the protein on the surface. The decrease in the observed resonant frequency reflects the presence of a visco-elastic protein layer at the interface, which will induce viscous losses resulting in an increase in the dissipation of electrical energy from the quartz crystal[9]. The energy is converted to thermal energy, which flows into the liquid environment in contact with the device in the form of an acoustic wave[10].

Now that it has been established that the device is sensitive to surface property changes in the oscillator (quartz disc), an on-line experiment is performed where the changes in frequency can be monitored as a function of time. The first step in this experiment was to generate a calibration curve using the resonance curve generated in FIG. 10. The steepest part of the curve is used in the analysis in order to ensure that any small change in the resonant frequency of the disc, caused by a change in the surface properties of the disc, will have a large effect on the impedance of the coil. Impedance of the coil serves as the analytical signal.

Figure 10:
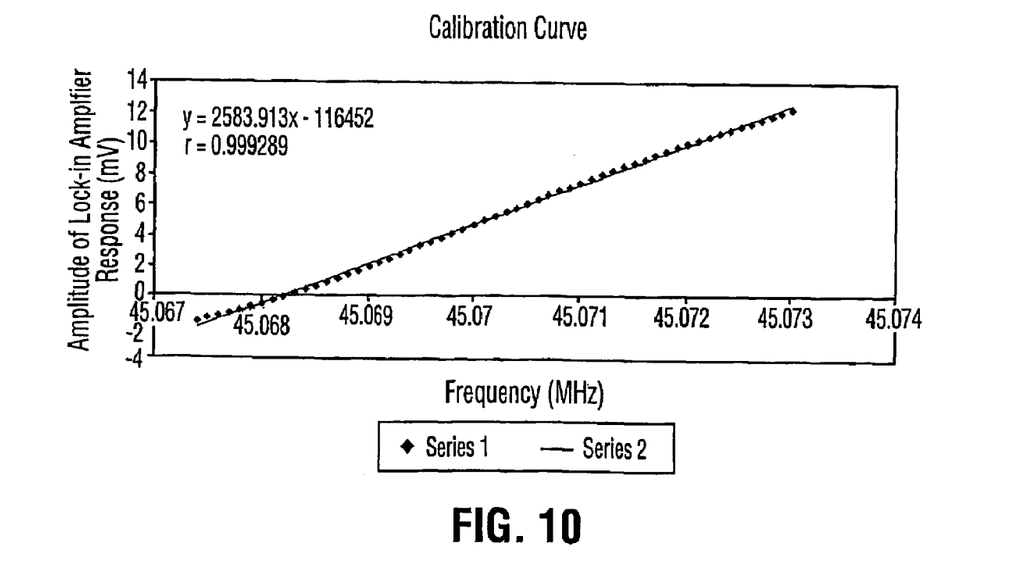
FIG. 10 is a calibration curve for use in on-line monitoring of neutravidin experiment.

FIG. 10 shows the calibration curve having the acquired data, series 1, along with the best fit line, series 2, generated from a least squares program. The r value shows a good correlation between the acquired data and the best fit line. The slope, m, and the y intercept, b, are the important parameters that are extracted from the best fit line, which are to be used in the on-line experiment.

Figure 11:
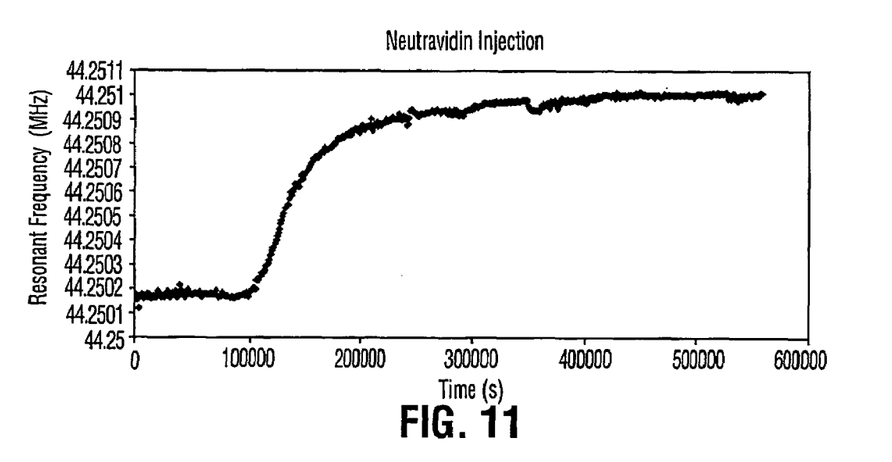
FIG. 11 illustrates the result of an on-line experiment involving the injection of neutravidin under flowing buffer.

FIG. 11 illustrates the result of an "on-line" experiment (e.g. performed in real time). Upon neutravidin injection, a frequency shift of approximately 800 Hz was observed which indicates the presence of the visco-elastic protein at the surface. Although the graph points to a frequency increase, FIG. 9 demonstrates that this is a minor deviation, as it should be a frequency decrease.

In order to reduce the baseline noise, and to possibly increase the received signal some modifications were made to the device, as discussed herein. In particular, the introduction of a capacitor before the detector serves to filter out extra background noise, while reducing the cut-off filter frequency allows more signal to get through to the detector, thereby making it more sensitive to impedance changes in the coil.

Figure 12:
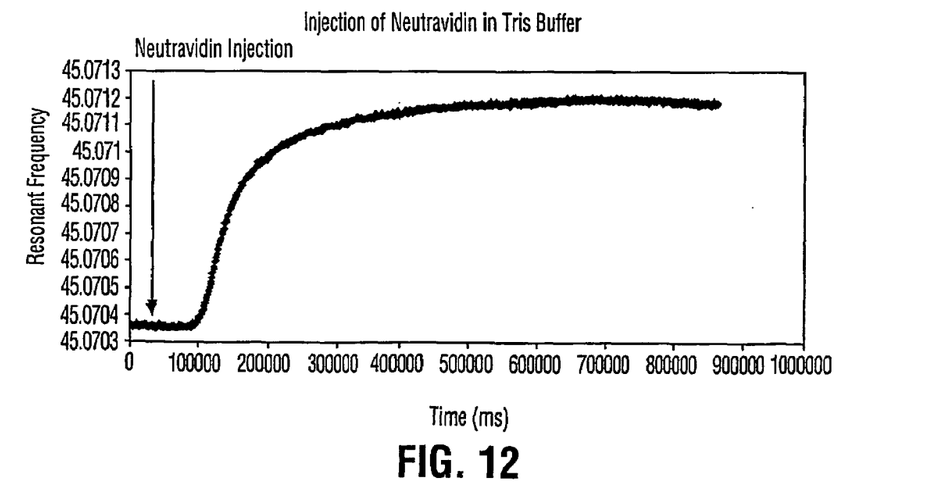
FIG. 12 illustrates the result of an on-line experiment involving neutravidin injection after circuit improvements.

FIG. 12 illustrates the results of these modifications, showing data obtained after neutravidin injection following circuit improvements. The frequency shift, as a result of neutravidin injection, is about 840 Hz. Though the frequency shift only appears to increase by 40 Hz, the standard deviation of the baseline is significantly reduced (from about 16 Hz down to about 5 Hz). The reduction in baseline noise results in the increase of the chemical signal to noise ratio, which leads to an increase in the sensitivity (lower limit of detection) of the device.

These results clearly indicate the advantages the sensor according to the invention has in its application to the study of biological phenomena at interfaces. The enormous shifts associated with the presence of neutravidin (800+ Hz) compared with the Transverse Shear Mode devices (200

Hz)[19], indicate that the limit of detection for the sensor according to the invention is greater than that of conventional sensing methodologies.

EXAMPLE 2

Methodology. Resonance envelopes were generated in air and liquid by soft clamping a crystal (an AT-cut quartz disc "blank", having no metal electrode thereon) in the flow through cell (internal volume approx. 70 μL). Resonance envelopes generated in liquid were acquired in Tris buffer (7.5 pH); prepared by adding 5 mL of 1mol/L Tris+7 mL 5 mol/L NaCl+0.2 mL of 0.5 mol/L EDTA+487.8 mL distilled water. Flow rates were maintained at approximately 0.6 mL/min. In this example, the field effect transistor is of the type shown in the schematic of FIG. 4B.

Protein injection experiments involved the use of neutravidin (non-glycosylated version of avidin). The neutravidin was dissolved in the tris buffer to make a 1 mg/mL solution. Buffer was flown through the cell for 10 minutes, then 500 μL of the neutravidin solution was injected, followed by flowing buffer. All experiments were conducted using 45 MHz carrier signal. Data was processed and displayed via NI Labview™ program software.

Figure 13:
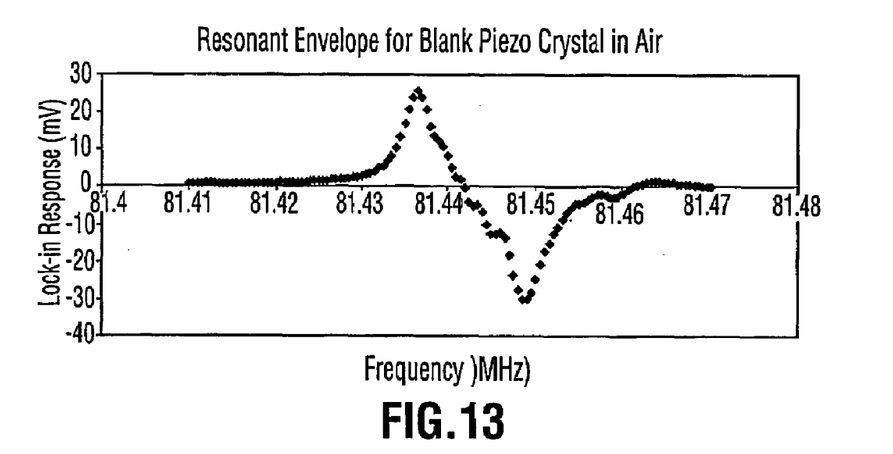
FIG. 13 illustrates a resonance envelope for a blank AT-cut quartz disc excited in air.
Figure 14:
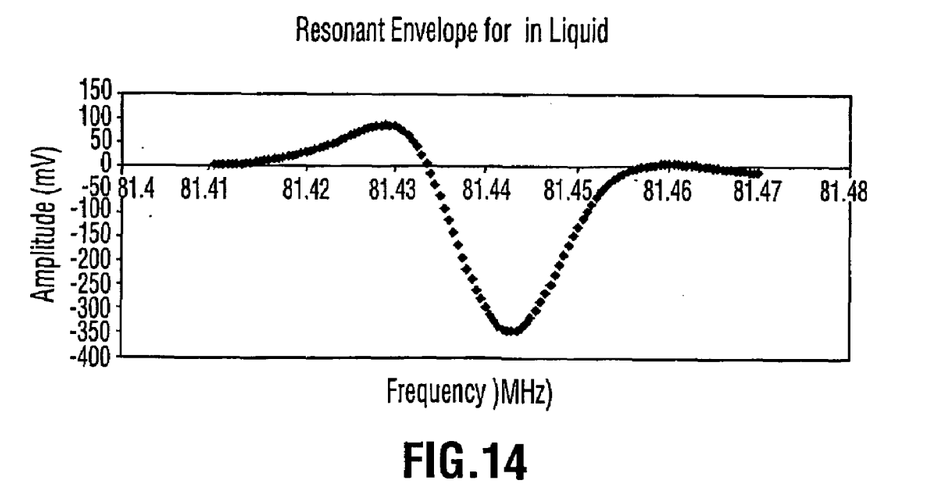
FIG. 14 illustrates a resonance envelope for a blank AT-cut quartz disc excited in an aqueous medium.

Results and Discussion. FIG. 13 shows the resonance envelope for a blank AT-cut Quartz disc excited in air. The shape of the envelope is not perfectly smooth indicating that more than one type of acoustic mode is being excited in the disc. However, upon immersing the disc in an aqueous medium, the envelope appears quite smooth, as shown in FIG. 14. Two possible explanations as to why this happens are that the different modes are being smeared together, or the pressure exerted by the liquid enhances a particular mode of resonance, while the others are suppressed. The envelope in liquid, compared for the same envelope in air, appears at lower frequencies due to coupling phenomena.

For the protein injection experiments, neutravidin was again used, as described in Example 1. Since the EMPAS device of this example employs blank piezoelectric crystals, neutravidin is simply adsorbed nonspecifically to the surface of the device.

Figure 15:
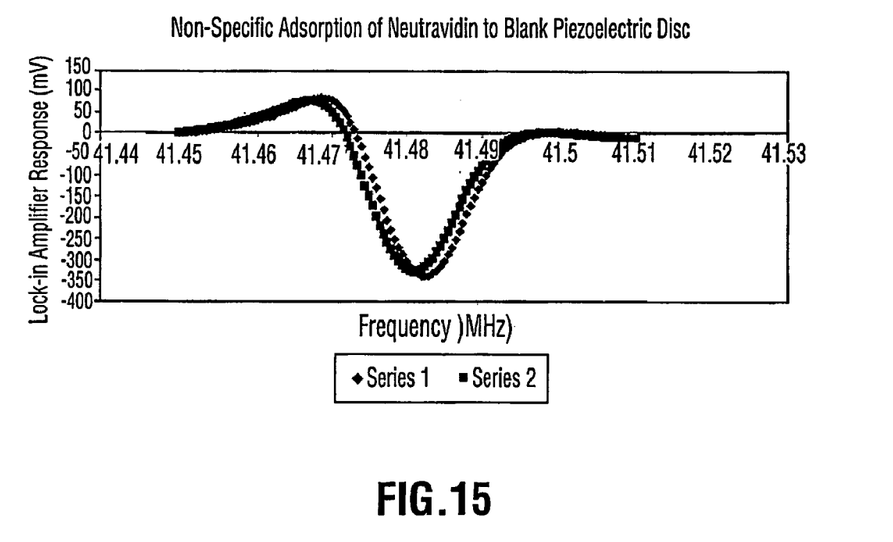
FIG. 15 illustrates resonance envelopes acquired with a blank AT-cut quartz disc before and after neutravidin injection.

FIG. 15 illustrates resonance envelopes acquired before and after neutravidin injection. Series 1 is the resonance envelope acquired under flowing buffer conditions only (no protein), while series two was acquired approximately 15 min. after protein injection. There is clearly a downward shift the resonance envelop as a result of the presence of the protein on the surface. The frequency decrease, in the observed resonant frequency reflects the presence of a visco-elastic protein layer at the interface, which induces viscous losses resulting in an increase in the dissipation of electrical energy from the quartz crystal[9]. The energy is converted to thermal energy, which flows into the liquid environment in contact with the device in the form of an acoustic wave[10]. The overall shift for the non-specifically adsorbed protein is around 1500 Hz.

The EMPAS device can also be used as a sensor by monitoring specific frequency changes, rather than monitoring the entire envelope. The inflection points of the curves illustrate the best way to do this. The signal generator sweeps a small region of the envelope, and once the inflection point of interest is found and the recorded, the generator then sweeps again and the process is continued. This "on-line" approach allows direct observation of changes, which closely represents "real-time".

Although an 81 MHz signal is used in this example, other frequencies may be used, as would be clear to one of skill in the art. By simply tuning the coil/capacitor circuit one can interrogate the disc using any multiple of its fundamental frequency. Impedance analyzer experiments have shown the device to work as high as 500 MHz. Thus EMPAS has capacity to provide an acoustic wave sensor in which the frequency shift depends linearly on the applied harmonic. Therefore a greater limit of detection may be obtained working at 100+ MHz, compared with conventional devices, which work at 9 MHz.

The above-described embodiments of the present invention are intended to be examples only. Alterations, modifications and variations may be effected to the particular embodiments by those of skill in the art without departing from the scope of the invention, which is defined solely by the claims appended hereto.

REFERENCES

1. D. Stone Lecture notes CHM414. University of Toronto. 2001.
2. G. L. Hayward, M. Thompson. A Transverse Shear Model of a Piezoelectric Chemical Sensor. *Journal of Applied Physics*. Vol. 83(4). 1998. pp 2194–2201.
3. G. L. Hayward, M. Thompson. A Transverse Shear Model of a Piezoelectric Chemical Sensor. *Journal of Applied Physics*. Vol. 83(4). 1998. pp 2194–2201.
4. W. G. Cady. Piezoelectricity vol.1. *Introduction to Theory and Applications of Electrochemical Phenomena in Crystals*. New York: Dover Publications Inc. 1964. pg. 81.
5. W. G. Cady. Piezoelectricity vol. 2. *Introduction to Theory and Applications of Electrochemical Phenomena in Crystals*. New York: Dover Publications Inc. 1964. pg. 759.
6. V. M. Ristic. Principles of Acoustic Wave Devices. Toronto: John Wiley and Sons. 1983. Pg. 127.
7. G. L. Hayward, M. Thompson. A Transverse Shear Model of a Piezoelectric Chemical Sensor. *Journal of Applied Physics*. Vol. 83(4). 1998. pp 2194–2201.
8. B. A. Cavic, F. L. Chu, L. M. Furtado, S. Gafouri, G. L. Hayward, D. P. Mack, M. E. McGovern, H. Su and M. Thompson Acoustic waves and the real-time study of biochemical macromolecules at the liquid/solid interface. *Faraday Discussions*. 107(1997). 169.
9. J. Rickert, G. L. Hayward, B. A. Cavic, M. Thompson, W. Gopel. Biosensors Based on Acoustic Waves Devices. *Article for Sensors update*. 1998. 3 of 43.
10. H. Su, S. Chong, M. Thomson. Interfacial Hybridization of RNA Homopolymers Studied by Liquid Phase Acoustic Network Analysis. *Langmuir*. 12(1996). 2251.

What is claimed is:

1. An acoustic wave sensor comprising a sensor plate formed of piezoelectric material, and an electromagnetic field fluctuator for inducing a fluctuating electromagnetic field in the piezoelectric material to cause acoustic wave vibration of the sensor plate.

2. The sensor of claim 1, wherein the electromagnetic field fluctuator comprises a coil through which AC current flows to induce a fluctuating electromagnetic field.

3. The sensor of claim 2, wherein the electromagnetic field fluctuator additionally comprises a magnet.

4. The sensor of claim 1, wherein the acoustic wave vibration of the sensor plate comprises vibration at a resonance frequency.

5. A biosensor comprising the sensor of claim 1 having a biomolecule bound to the sensor plate.

6. The biosensor according to claim 4 wherein said biomolecule is bound to the sensor plate by a means selected from the group consisting of tethering, covalent binding, non-covalent adhesion, adsorption, and ionic bonding.

7. A method of evaluating interaction of a biomolecule with a piezoelectric sensor plate comprising:
   imparting a fluctuating electromagnetic field to the piezoelectric sensor plate so as to vibrate the plate at a resonance frequency;
   exposing the sensor plate to a composition suspected of containing the biomolecule; and
   evaluating changes in vibration of the piezoelectric sensor plate caused by interaction of the biomolecule with the sensor plate.

8. A method of evaluating biomolecular interaction of a probe with a target comprising:
   binding the probe to a sensor plate formed of piezoelectric material,
   imparting a fluctuating electromagnetic field to the sensor plate so as to vibrate the sensor plate at a resonance frequency;
   exposing the sensor plate to a composition suspected of containing the target; and
   evaluating changes in vibration of the sensor plate caused by interaction of the probe with the target.

* * * * *